US009265769B2

(12) United States Patent
Pellicciari et al.

(10) Patent No.: US 9,265,769 B2
(45) Date of Patent: *Feb. 23, 2016

(54) THIAZOLYL- AND OXAZOLYL-ISOQUINOLINONES AND METHODS FOR USING THEM

(71) Applicants: Roberto Pellicciari, Perugia (IT); Flavio Moroni, Florence (IT)

(72) Inventors: Roberto Pellicciari, Perugia (IT); Flavio Moroni, Florence (IT); Adam Gilbert, Guilford, CT (US)

(73) Assignees: Roberto Pellicciari, Perugia (IT); Flavio Moroni, Florence (IT)

( * ) Notice: Subject to any disclaimer, the term of this patent is extended or adjusted under 35 U.S.C. 154(b) by 0 days.

This patent is subject to a terminal disclaimer.

(21) Appl. No.: 14/535,877

(22) Filed: Nov. 7, 2014

(65) Prior Publication Data

US 2015/0133443 A1    May 14, 2015

Related U.S. Application Data

(60) Continuation of application No. 13/655,082, filed on Oct. 18, 2012, now Pat. No. 8,906,935, which is a division of application No. 12/487,247, filed on Jun. 18, 2009, now Pat. No. 8,299,090.

(60) Provisional application No. 61/073,857, filed on Jun. 19, 2008.

(51) Int. Cl.
*A61K 31/5377* (2006.01)
*A61K 31/4745* (2006.01)
*A61K 31/437* (2006.01)
*C07D 513/04* (2006.01)

(52) U.S. Cl.
CPC ........... *A61K 31/5377* (2013.01); *A61K 31/437* (2013.01); *A61K 31/4745* (2013.01); *C07D 513/04* (2013.01)

(58) Field of Classification Search
CPC . C07D 513/04; A61K 31/437; A61K 31/5377
USPC ...................... 546/83, 84; 514/293
See application file for complete search history.

(56) References Cited

U.S. PATENT DOCUMENTS

| 4,232,017 | A | 11/1980 | Winters et al. |
| 6,989,388 | B2 | 1/2006 | Pellicciari et al. |
| 7,501,412 | B2 | 3/2009 | Fujio et al. |
| 8,299,090 | B2 * | 10/2012 | Pellicciari et al. ............ 514/293 |
| 8,906,935 | B2 * | 12/2014 | Pellicciari et al. ............ 514/293 |
| 2005/0171101 | A1 | 8/2005 | Yamamoto et al. |
| 2009/0325951 | A1 | 12/2009 | Pellicciari et al. |

FOREIGN PATENT DOCUMENTS

| EP | 2303895 B1 | 9/2014 |
| WO | WO 02/36599 A1 | 5/2002 |
| WO | WO 2004/048339 A1 | 6/2004 |
| WO | WO 2007/149907 A3 | 2/2008 |

OTHER PUBLICATIONS

Chiarugi et al. "Novel Isoquinolinone-Derived Inhibitors of Poly(ADP-Ribose) Polymerase-1: Pharmacological Characterization and Neuroprotective Effects in an In Vitro Model of Cerebral Ischemia", *J. Pharmacol. Exp. Ther.*, 305.3(2003):943-949.
Dorwald, F.A. "Side Reactions in Organic Synthesis", Wiley: VCH, Weinheim (2005), p. IX of Preface.
Graziani et al. "Clinical Perspectives of PARP Inhibitors", *Pharmacological Research*, 52.1 (2005), 109-118.
Pellicciari, R. et al. "Towards new neuroprotective agents: design and synthesis of 4H-thieno [2,3-c] isquinolin-5-one derivatives as potent PARP-1 inhibitors", *Il Farmaco*, 58 (2003), pp. 851-858.
Summerfield, S. G. et al. "Central Nervous System Drug Disposition: The Relationship between in Situ Brain Permeability and Brain Free Fraction", *The Journal of Pharmacology and Experimental Therapeutics*, 322.1 (2007) : 205-213.
Tietze, L. F. and Lohmann, J.K. "Synthesis of Novel Chiral Thiophene-, Benzothiophene-and Benzofuran-Oxazoline Ligands and their Use in the Enantioselective Pd-Catalyzed Allylation", *Synlett*, No. 12, (2002), pp. 2083-2085.
Wermuth, C.G. "Molecular Variations Based on Isosteric Replacements", *Practice of Medicinal Chemistry*, (1996) : 203-237 XP002190259.
Yamaguchi, K. "4-Phenylthiazole Derivatives Inhibit II-6 Secretion in Osteoblastic Cells and Suppress Bone Weight Loss in Ovarlectomized Mice", *Bioorganic & Medicinal Chemistry Letters*, 9 (1999) : 957-960.

* cited by examiner

*Primary Examiner* — Rita Desai
(74) *Attorney, Agent, or Firm* — Cooley LLP; Ivor R. Elrifi; Heidi A. Erlacher

(57) ABSTRACT

The present invention relates to substituted thiazolyl- and oxazolyl-isoquinolinones that act, for example, as modulators of poly(ADP-ribose) polymerase (PARP). The present invention also relates to processes for the preparation of substituted thiazolyl- and oxazolyl-isoquinolinones and to their use in treating various diseases and disorders.

13 Claims, No Drawings

THIAZOLYL- AND OXAZOLYL-ISOQUINOLINONES AND METHODS FOR USING THEM

This application is a continuation of U.S. application Ser. No. 13/655,082 (now allowed) filed Oct. 18, 2012 which is a divisional of U.S. application Ser. No. 12/487,247 (U.S. Pat. No. 8,299,090), filed Jun. 18, 2009, and claims the benefit under 35 U.S.C. §119(e) to U.S. Provisional Application No. 61/073,857, filed Jun. 19, 2008, which are incorporated herein by reference in their entireties.

FIELD

The present invention relates to substituted thiazolyl- and oxazolyl-isoquinolinones that act, for example, as modulators of poly(ADP-ribose) polymerase (PARP). The present invention also relates to processes for the preparation of substituted thiazolyl and oxazolyl-isoquinolinones and to their use in treating various diseases and disorders.

BACKGROUND

The poly (ADP-ribose) polymerase (PARP) family of enzymes catalyzes the post-translational modification of several nuclear proteins in response to DNA damage. PARP activation is involved in the ability of cells to repair injured DNA, yet also plays a role in the pathogenesis of various cardiovascular and inflammatory diseases. The family of PARP enzymes contains at least 5 members, termed PARP-1, PARP-2, PARP-3, tankyrase, and VPARP.

Because of PARP's role in DNA repair, and the pathogenesis of various cardiovascular and inflammatory diseases, a number of PARP inhibitors are being currently developed clinically or are already in clinical trials for the treatment of various diseases and conditions, including chronic and acute neurological and cardiovascular conditions and cancers. (Pharmacological Research Vol: 52 Issue: 1, July, 2005 pp: 109-118). A need exists for potent compounds that can inhibit PARP activity. The present invention addresses this and other needs.

SUMMARY

The present invention is directed to certain substituted thiazolyl- and oxazolyl-isoquinolinones and to their use, for example, in medical treatment. In one aspect, the invention relates to substituted thiazolyl- and oxazolyl-isoquinolinones that act as modulators of PARP. The compounds can be used as PARP inhibitors to, for example, inhibit neuronal cell death in a subject. The compounds can be used, for example, to treat disease and disorders including damage due to ischemia and reperfusion, degenerative diseases, inflammation, including multiple inflammatory disease, tumor diseases, including cancer, and cardiovascular dysfunction, including myocardial infarction and atherosclerosis.

In certain aspects, the present invention is directed to compounds of Formula I:

Formula I wherein:
X is $C_1$-$C_9$ alkylene, $C_2$-$C_9$ alkenylene, or $C_2$-$C_9$ alkynylene;
Y is O or S;
$R^1$, $R^2$, $R^3$, and $R^4$ are independently selected from hydrogen, $C_1$-$C_6$ alkyl, halogen, hydroxy, $NH_2$, CN, $C_1$-$C_6$ perfluoroalkyl, $CO_2H$, $OR^7$, $COOR^7$, or $NHR^7$;
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl, wherein the alkyl, alkenyl and rings of the cycloalkyl, phenyl and benzyl groups are optionally substituted with one or more groups (e.g. 1 to 3, 1 to 2 or 1) independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen; or
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms independently selected from N, O, or S, the remainder of the ring atoms being carbon atoms;
$R^7$ is $C_1$-$C_6$ alkyl, $C_2$-$C_6$ alkenyl, or $C_3$-$C_7$ cycloalkyl wherein the alkyl, alkenyl, and rings of the cycloalkyl are optionally substituted with one or more groups (e.g. 1 to 3, 1 to 2 or 1) independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen;
or a pharmaceutically acceptable salt form thereof.

In other embodiments, the invention relates to compositions comprising at least one compound of the present invention and at least one pharmaceutically acceptable carrier.

In yet other embodiments, the invention is directed to methods for treating a patient having tissue damage due to ischemia and/or reperfusion; methods for treating diseases associated with tissue damage due to ischemia and/or reperfusion, including, for example, stroke, cerebral or spinal trauma, epileptic events, cerebral damage due to cardiac arrest and/or conditions arising from situations of prolonged hypotension, respiratory arrest, carbon monoxide or cyanide poisoning, drowning, or hydrocephalus; methods for treating degenerative diseases of the central nervous system, including, for example, Parkinson's disease, Alzheimer's dementia, Huntington's chorea, amyotrophic lateral sclerosis, macular degeneration and retinal ischemia; methods for treating degenerative diseases of the muscles, including, for example, muscular dystrophy; methods for treating degenerative diseases of the bones, including, for example, osteoporosis; methods for treating degenerative diseases of the vascular system, including, for example, atherosclerosis, diabetes, and diseases of the immune system present during senescence; methods for treating inflammatory diseases, including, for example, multiple sclerosis and other demyelinizing diseases, Guillain-Barre syndrome, neuralgias of the trigeminus and/or other cranial nerves, peripheral neuropathies and other chronic pain, osteoarthritis, inflammatory diseases of the intestine including, for example, Crohn's disease, ulcerative colitis, and other forms of colitis; and methods for the treatment of various forms of cancer including, for example, leukemia, sarcoma primary or associated with AIDS, breast cancer, refractory solid tumors, lymphoid malignancies, brain tumors, and p53 deficient tumors.

DETAILED DESCRIPTION

The present invention is directed to, inter alia, substituted thiazolyl- and oxazolyl-isoquinolinones and to their use as modulators of PARP. The compounds can be used to inhibit PARP. The compounds can also be used in medical treatment to treat various disease and disorders, including those associated with neuronal cell death.

The following definitions are provided for the full understanding of terms used herein.

The term "alkyl," as used herein, whether used alone or as part of another group, refers to an aliphatic hydrocarbon chain having 1 to 12 carbon atoms, preferably 1 to 8 carbon atoms, more preferably 1 to 6 carbon atoms, and more preferably 1 to 4 or 1 to 3 carbon atoms. The term "alkyl" includes straight and branched chains. Examples of alkyl groups include methyl, ethyl, n-propyl, isopropyl, n-butyl, isobutyl, sec-butyl, t-butyl, n-pentyl, isopentyl, neo-pentyl, n-hexyl, and isohexyl groups.

As used herein, the term "alkylene" refers to a bivalent alkyl radical having the general formula —$(CH_2)_n$—, where n is 1 to 10, and all combinations and subcombinations of ranges therein. The alkylene group may be straight, branched or cyclic. Non-limiting examples include methylene, methylene (—$CH_2$—), ethylene (—$CH_2CH_2$—), propylene (—$(CH_2)_3$—), trimethylene, pentamethylene, and hexamethylene. Preferred alkylene groups have from 1 to about 3 carbons.

The term "perfluoroalkyl," as used herein, refers to a straight or branched aliphatic hydrocarbon chain of 1 to 8 carbon atoms and preferably 1 to 3 carbon atoms, in which all hydrogens are replaced with fluorine e.g $CF_3$.

The term "alkenyl," as used herein, refers to an aliphatic straight or branched hydrocarbon chain having 2 to 12 carbon atoms that contains 1 to 3 double bonds. Examples of alkenyl groups include, but are not limited to, vinyl, prop-1-enyl, allyl, but-1-enyl, but-2-enyl, but-3-enyl, 3,3-dimethylbut-1-enyl, or 2-methylvinyl.

As used herein, the term "alkenylene" refers to an alkylene group containing at least one carbon-carbon double bond. Exemplary alkenylene groups include, for example, ethenylene (—CH═CH—) and propenylene (—CH═CHCH$_2$—). Preferred alkenylene groups have from 2 to about 3 carbons.

The term "alkynyl," as used herein, refers to an aliphatic straight or branched hydrocarbon chain having 2 to 9 carbon atoms that contains 1 to 3 triple bonds.

As used herein, the term "alkynylene" refers to an alkylene group containing at least one carbon-carbon triple bond. Exemplary alkynylene groups include, for example, acetylene (—C≡C—), propargyl (—CH2C≡C—), and 4-pentynyl (—CH2CH2CH2C≡CH—). Preferred alkynylene groups have from 2 to about 3 carbons.

The term "heterocyclic ring," as used herein, refers to a 3 to 12 membered, and more preferably 5 to 7 membered, saturated, partially unsaturated, or unsaturated monocyclic or bicyclic ring system which contains carbon ring atoms and from 1 to 4 ring heteroatoms independently selected from nitrogen, oxygen, or sulfur. The nitrogen and sulfur heteroatoms may optionally be oxidized. Heterocyclic rings include, for example, 3 to 12 membered saturated monocylic rings such as piperidine, morpholine, pyrrolidine, homopiperidine, aziridine, and azetidine.

The term "cyano," as used herein, refers to the group —CN.
The term "amino," as used herein, refers to the group —$NH_2$.

The terms "halogen" or "halo," as used herein, refer to chlorine, bromine, fluorine or iodine.

The compounds of the present invention can also be solvated, especially hydrated. Hydration can occur, for example, during manufacturing of the compounds or compositions comprising the compounds, or the hydration can occur, for example, over time due to the hygroscopic nature of the compounds. The skilled artisan will understand that the phrase "compound of Formula I," as used herein, is meant to include solvated compounds of Formula I.

The term "therapeutically effective amount," as used herein, refers to the amount of a compound of the present invention that, when administered to a patient, is effective to at least partially treat a condition from which the patient is suffering or is suspected to suffer.

The term "pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts" refers to salts that are pharmaceutically acceptable and have the desired pharmacological properties. Such salts include, for example, salts that can be formed where acidic protons present in the compounds are capable of reacting with inorganic or organic bases. Suitable inorganic salts include, for example, those formed with the alkali metals or alkaline earth metals, e.g. sodium and potassium, magnesium, calcium, and aluminum. Suitable organic salts include, for example, those formed with organic bases such as the amine bases, e.g. ethanolamine, diethanolamine, triethanolamine, tromethamine, N-methylglucamine, and the like. Pharmaceutically acceptable salts can also include acid addition salts formed from the reaction of amine moieties in the parent compound with inorganic acids and organic acids including the alkane- and arene-sulfonic acids (e.g. acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable organic and inorganic acids).

The terms "inhibitor," "activator," and "modulator" as used in connection with expression or activity refer to inhibitory, activating, or modulating molecules, respectively. Inhibitors of the present invention include compounds or compositions that inhibit expression of PARP or bind to, partially or totally block stimulation, decrease, prevent, delay activation, inactivate, desensitize, or down regulate the activity of PARP. Samples or assays comprising PARP can be treated with a composition of the present invention and compared to control samples without a composition of the present invention. Control samples (untreated with compositions of the present invention) can be assigned a relative activity value of 100%. In certain embodiments, inhibition of PARP is achieved when the activity value relative to the control is about 80% or less.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects such as nausea, dizziness, gastric upset and the like which would be to a degree that would prohibit administration of the compound.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and formulations of the present invention.

The terms "administer," "administering," or "administration," as used herein, refer to either directly administering a compound or composition to a patient, or administering a prodrug derivative or analog of the compound to the patient, which will form an equivalent amount of the active compound or substance within the patient's body.

The terms "treat" and "treating," as used herein, refer to partially or completely alleviating, inhibiting, preventing, ameliorating and/or relieving a condition from which a patient is suspected to suffer.

The terms "suffer" and "suffering," as used herein, refer to one or more conditions with which a patient has been diagnosed, or is suspected to have.

In certain aspects, the present invention is directed to compounds of Formula I:

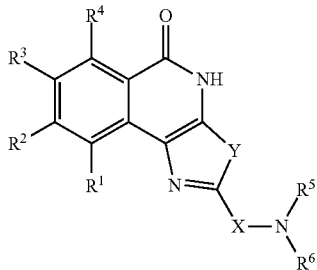

Formula I wherein:

X is $C_1$-$C_9$ alkylene, $C_2$-$C_9$ alkenylene, or $C_2$-$C_9$ alkynylene;

Y is O or S;

$R^1$, $R^2$, $R^3$, and $R^4$ are independently selected from hydrogen, $C_1$-$C_6$ alkyl, halogen, hydroxy, $NH_2$, CN, $C_1$-$C_6$ perfluoroalkyl, $CO_2H$, $OR^7$, $COOR^7$, or $NHR^7$;

$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl, wherein the alkyl, alkenyl and rings of the cycloalkyl, phenyl and benzyl groups are optionally substituted with one or more groups (e.g. 1 to 3, 1 to 2 or 1) independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen; or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms independently selected from N, O, or S, the remainder of the ring atoms being carbon atoms;

$R^7$ is $C_1$-$C_6$ alkyl, $C_2$-$C_6$ alkenyl, or $C_3$-$C_7$ cycloalkyl wherein the alkyl, alkenyl, and rings of the cycloalkyl are optionally substituted with one or more groups (e.g. 1 to 3, 1 to 2 or 1) independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, or halogen;

or a pharmaceutically acceptable salt form thereof.

Such substituted thiazolyl- and oxazolyl-isoquinolinones acids include the compounds of formulas II, III, and IV:

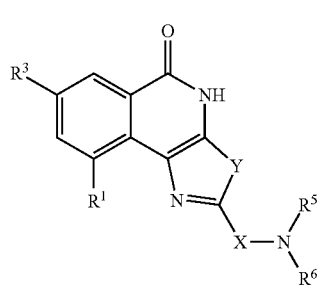

Formula II

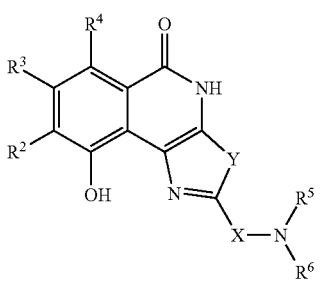

Formula III

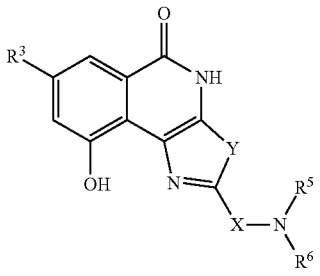

Formula IV wherein X, Y, $R^1$, $R^2$, $R^3$, $R^4$, $R^5$, and $R^6$ are as defined herein; or a pharmaceutically acceptable salt thereof.

In certain embodiments $R^1$, $R^2$, $R^3$, and $R^4$ are independently hydrogen, halogen, hydroxyl, $NH_2$, $C_1$-$C_6$ alkoxy, CN, or $C_1$-$C_6$ perfluroalkyl.

$R^3$ may suitably be hydrogen or halogen. In certain embodiments $R^3$ is hydrogen.

In certain embodiments $R^5$ and $R^6$ are each independently hydrogen, $C_1$-$C_6$ alkyl, $C_2$-$C_4$ alkenyl, $C_3$-$C_7$ cycloalkyl, phenyl or benzyl.

Suitably one or both or $R^5$ and $R^6$ may be $C_1$-$C_6$ alkyl which may be the same or different.

In certain embodiments X is $C_1$-$C_3$ alkylene $C_2$-$C_3$alkenylene or $C_2$-$C_3$ alkynylene.

When $R^5$ and $R^6$ form a ring together with the nitrogen to which they are attached the ring may suitably be piperidine, morpholine, pyrrolidine, homopiperidine, aziridine or azetidine.

Compounds of Formulas I, II, III, and IV include those in which:

X is $C_1$-$C_9$ alkylene, $C_2$-$C_9$ alkenylene, or $C_2$-$C_9$ alkynylene;

Y is O or S;

$R^1$, $R^2$, $R^3$, and $R^4$ are, independently, hydrogen, halogen, hydroxy, $NH_2$, $C_1$-$C_6$ alkoxy, CN, or $C_1$-$C_6$ perfluoroalkyl;

$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt form thereof.

Compounds of Formulas I, II, III, and IV further include those in which:
X is $C_1$-$C_3$ alkylene, $C_2$-$C_3$ alkenylene, or $C_2$-$C_3$ alkynylene;
Y is O or S;
$R^1$, $R^2$, $R^3$, and $R^4$ are, independently, hydrogen, halogen, hydroxy, $NH_2$, $C_1$-$C_6$ alkoxy, CN, or $C_1$-$C_6$ perfluoroalkyl;
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen or halogen;
Y is O;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt form thereof.

Compounds of Formulas I, II, III, IV, V, or VI further include those in which:
$R^1$, $R^2$, $R^4$, and $R^7$ are as defined herein;
$R^3$ is hydrogen or halogen;
Y is S;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen;
Y is O;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen;
Y is S;
X is $C_1$-$C_9$ alkylene, $C_2$-$C_9$ alkenylene, or $C_2$-$C_9$ alkynylene; and
$R^5$ and $R^6$ are each, independently, hydrogen, $C_1$-$C_6$ alkyl, $C_2$-$C_4$ alkenyl, $C_3$-$C_7$ cycloalkyl, phenyl, or benzyl or $R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen, halogen, hydroxy, $NH_2$, $C_1$-$C_6$ alkoxy, CN, or $C_1$-$C_6$ perfluoroalkyl;
Y is O;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen, halogen, hydroxy, $NH_2$, $C_1$-$C_6$ alkoxy, CN, or $C_1$-$C_6$ perfluoroalkyl;
Y is S;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen or halogen;
Y is O;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen or halogen;
Y is S;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen;
Y is O;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen;
Y is S;
X is $C_1$-$C_9$ alkylene, $C_2$-$C_9$ alkenylene, or $C_2$-$C_9$ alkynylene; and
$R^5$ and $R^6$ are each, independently, $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen or halogen;
Y is O or S;
X is $C_1$-$C_9$ alkylene, $C_2$-$C_9$ alkenylene, or $C_2$-$C_9$ alkynylene; and
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms. In certain aspects, the heterocyclic ring is a 3 to 12 membered saturated monocylic ring such as piperidine, morpholine, pyrrolidine, homopiperidine, aziridine, or azetidine; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen;
Y is O or S;
X is $C_1$-$C_9$ alkylene, $C_2$-$C_9$ alkenylene, or $C_2$-$C_9$ alkynylene; and
$R^5$ and $R^6$ together with the nitrogen to which they are attached form a saturated, partially unsaturated, or unsaturated 3 to 12 membered monocylic or bicyclic heterocyclic ring optionally comprising from one to three additional ring heteroatoms selected from N, O, or S, the remainder of the ring atoms being carbon atoms. In certain aspects, the heterocyclic ring is a 3 to 12 membered saturated monocylic ring such as piperidine, morpholine, pyrrolidine, homopiperidine, aziridine, or azetidine; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen or halogen;
Y is S; and
$R^5$ and $R^6$ are each, independently $C_1$-$C_6$ alkyl; or a pharmaceutically acceptable salt form thereof.

Compounds of Formulas I, II, III, and IV further include those in which:
$R^1$, $R^2$, $R^4$, and $R^7$ are as defined herein;
$R^3$ is hydrogen;
Y is S; and
$R^5$ and $R^6$ are each, independently $C_1$-$C_6$ alkyl; or a pharmaceutically acceptable salt form thereof.

In exemplary embodiments, halogen is fluorine.
In exemplary embodiments, X is $C_1$-$C_3$ alkylene, $C_2$-$C_3$ alkenylene, or $C_2$-$C_3$ alkynylene.
Exemplary compounds of Formula 1 include:
2-[(Dimethylamino)methyl[1,3]thiazolo[5,4-c]isoquinolin-5(4H)-one;
2-[3-(Dimethylamino)prop-1-yn-1-yl][1,3]thiazolo[5,4-c]isoquinolin-5(4H)-one;
2-(2-(Dimethylamino)ethyl)thiazolo[5,4-c]isoquinolin-5(4H)-one;
2-((Dimethylamino)methyl)-9-hydroxythiazolo[5,4-c]isoquinolin-5(4H)-one;
9-Hydroxy-2-(morpholin-4-ylmethyl)[1,3]thiazolo[5,4-c]isoquinolin-5(4H)-one;
9-Hydroxy-2-(piperidin-1-ylmethyl)[1,3]thiazolo[5,4-c]isoquinolin-5(4H)-one;
9-Hydroxy-2-(pyrrolidin-1-ylmethyl)[1,3]thiazolo[5,4-c]isoquinolin-5(4H)-one;
2-{[(3R)-3-(dimethylamino)pyrrolidin-1-yl]methyl}-9-hydroxy[1,3]thiazolo[5,4-c]isoquinolin-5(4H)-one;
9-Hydroxy-2-(octahydroquinolin-1(2H)-ylmethyl)[1,3]thiazolo[5,4-c]isoquinolin-5(4H)-one;
2-{[(2R,6S)-2,6-Dimethylmorpholin-4-yl]methyl}-9-hydroxy[1,3]thiazolo[5,4-c]isoquinolin-5(4H)-one;
9-Hydroxy-2-[(2-methylpyrrolidin-1-yl)methyl][1,3]thiazolo[5,4-c]isoquinolin-5(4H)-one;
9-Hydroxy-2-{[(2R)-2-(trifluoromethyl)pyrrolidin-1-yl]methyl}[1,3]thiazolo[5,4-c]isoquinolin-5(4H)-one; and
2-{[2R,6S)-2,6-Dimethylpiperidin-1-yl]methyl}-9-hydroxy[1,3]thiazolo[5,4-c]isoquinolin-5(4H)-one; or a pharmaceutically acceptable salt form thereof.

In certain embodiments, the pharmaceutically acceptable salt of a compound of Formula I is a hydrochloride or hydrobromide salt.

In some embodiments, compounds of the present invention can be used to modulate the activity of PARP. Such compounds are of interest for the treatment of a variety of disease and conditions. In certain embodiments, for example, they can be administered to a subject for the treatment of tissue damage due to ischemia and reperfusion. Such damage, with consequent apoptopic or necrotic cell death, can give rise to various neurological diseases such as, for example, stroke, cerebral or spinal trauma, epileptic events, cerebral damage due to cardiac arrest and/or to situations of prolonged hypotension, respiratory arrest, carbon monoxide or cyanide poisoning, drowning or hydrocephalus. The cerebral insult can also be of a toxic nature (excitotoxins and other chemical products), iatrogenic (including surgical) and due to ionizing radiation. Tissue damage due to ischemia and reperfusion can also affect the myocardium and be present in many cardiopathies such as post-infarction, during and after coronary by-pass surgery, on the resumption of perfusion in transplanted hearts and indeed any time when for surgical reasons cardiac arrest is performed, and blood reperfusion is initiated. The kidney, the liver, the intestine and skeletal musculature are susceptible to damage due to ischemia and reperfusion. This can occur in septic, endotoxic, hemorrhagic and compression shock. It also occurs in strangulated hernia, strangulation of intestinal loops, and after prolonged compression of joints in multiply traumatized patients.

In some embodiments, compounds of the present invention can be administered to a subject for the treatment of degenerative diseases. The inhibition of PARP can extend the reproductive capacity of various cells and be utilized to prevent diseases typically associated with aging. Exemplary degenerative diseases include those of the central nervous system such as, for example, Parkinson's disease, Alzheimer's dementia, Huntington's chorea, amyotrophic lateral sclerosis, macular degeneration and retinal ischemia. Other degenerative diseases include, for example, the aging of the skin, degenerative diseases of the muscles (muscular dystrophy), bones (osteoporosis) and vascular system (atherosclerosis), diabetes and diseases of the immune system present during senescence.

In some embodiments, compounds of the present invention can be administered to a subject for the treatment of inflammatory diseases. Excessive activation of PARP can be harmful in various diseases of predominantly inflammatory nature, both of the central nervous system and of peripheral organs. Compounds of the invention can thus be useful in the following pathological situations: multiple sclerosis and other demyelinizing diseases, Guillain-Barre syndrome, neuralgias of the trigeminus and/or other cranial nerves, peripheral neuropathies and other chronic pain, osteoarthritis, and inflammatory diseases of the intestine (Crohn's disease, ulcerative colitis, and other forms of colitis).

In some embodiments, compounds of the present invention can be administered to a subject for the treatment of tumor diseases. PARP inhibitors can facilitate the death of tumor cells induced by ionizing agents or by chemotherapeutic agents and can be used, both alone and in combination with other treatments, in the prevention and in the therapy of various forms of cancer, for example, leukemia and/or sarcoma, whether these are primary or associated with AIDS, breast cancer, refractory solid tumors, lymphoid malignancies, brain tumors, and p53 deficient tumors. PARP inhibitors of the present invention can act to enhance the cytotoxicity of antitumor agents. For example, in certain embodiments, PARP inhibitors will act to enhance the cytotoxicity of topoisomerase I and II inhibitors, and alkylating agents including, for example, temozolomide.

In some embodiments, compounds of the present invention can be administered to a subject for the treatment of cancers including, for example, cancers of the female reproductive organs including, for example, ovarian cancer, cervical cancer and uterine cancer; lung cancer; breast cancer; renal cell carcinoma; Hodgkin's lymphoma; Non-Hodgkin's lymphoma; cancers of the genitourinary system including, for example, kidney cancer, prostate cancer, bladder cancer, and urethral cancer; cancers of the head and neck; liver cancer; cancers of the gastrointestinal system including, for example, stomach cancer, esophageal cancer, small bowel cancer or colon cancer; cancers of the biliary tree; pancreatic cancer; cancers of the male reproductive system including, for example, testicular cancer; Gestational trophoblastic disease; cancers of the endocrine system including, for example, thyroid cancer, parathyroid cancer, adrenal gland cancer, carcinoid tumors, insulinomas and PNET tumors; sarcomas, including, for example, Ewing's sarcoma, osteosarcoma, liposarcoma, leiomyosarcoma, and rhabdomyosarcoma; mesotheliomas; cancers of the skin; melanomas; cancers of the central nervous system; pediatric cancers; and cancers of the hematopoietic system including, for example, all forms of leukemia, myelodysplastic syndromes, myeloproliferative disorders and multiple myeloma.

In some embodiments, compounds of the present invention can be administered to a subject for the treatment of bone fractures as well as bone disorders, including osteoporosis, and for the treatment of arthritis, chronic obstructive pulmonary disease, cartilage defects, leiomyoma, acute myeloid leukemia, wound healing, prostate cancer, autoimmune inflammatory disorders, such as Graves ophthalmopathy, and combinations thereof.

In some embodiments, compounds of the present invention can be administered to a subject for the treatment of retinal degeneration and axotomy.

In some embodiments, compounds of the present invention can be administered to a subject for the treatment of cardiovascular dysfunction, including myocardial infarction and atherosclerosis.

In some embodiments, compounds of the present invention can be administered to a subject following a partial or complete artery occlusion in order to reduce brain damage. The compounds can be administered immediately after the occlusion or even with a significant delay after artery occlusion. For example, in certain embodiments, administration will start 1 to 10 hours (i.e., 1, 2, 3, 4, 5, 6, 7, 8, 9, or 10 hours) after artery occlusion, preferably 1 to 4 hours after artery occlusion.

In certain embodiments, the present invention therefore provides methods of treating, preventing, inhibiting, or alleviating each of the maladies listed above in a mammal, preferably in a human, comprising administering a therapeutically effective amount of a compound of the present invention to a patient suspected to suffer from such a malady.

In certain embodiments, the invention relates to compositions comprising at least one compound of the present invention and one or more pharmaceutically acceptable carriers, excipients, or diluents. In certain embodiments, the compositions comprise mixtures of one or more compounds of the present invention.

Certain of the compounds of the present invention contain stereogenic carbon atoms or other chiral elements and thus give rise to stereoisomers, including enantiomers and diastereomers. The invention generally relates to all stereoisomers of the compounds of Formula I, II, III or IV, as well as to mixtures of the stereoisomers. Throughout this application, the name of a compound without indication as to the absolute configuration of an asymmetric center is intended to embrace the individual stereoisomers as well as mixtures of stereoisomers. Reference to optical rotation [(+), (−) and (±)] is utilized to distinguish the enantiomers from one another and from the racemate. Furthermore, throughout this application, the designations R* and S* are used to indicate relative stereochemistry, employing the Chemical Abstracts convention which automatically assigns R* to the lowest numbered asymmetric center.

An enantiomer can, in some embodiments of the invention, be provided substantially free of the corresponding enantiomer. Thus, reference to an enantiomer as being substantially free of the corresponding enantiomer indicates that it is isolated or separated via separation techniques or prepared so as to be substantially free of the corresponding enantiomer. "Substantially free," as used herein, means that a significantly lesser proportion of the corresponding enantiomer is present. In preferred embodiments, less than about 90% by weight of the corresponding enantiomer is present relative to desired enantiomer, more preferably less than about 1% by weight. Preferred enantiomers can be isolated from racemic mixtures by any method known to those skilled in the art, including high performance liquid chromatography (HPLC), and the formation and crystallization of chiral salts, or preferred enantiomers, can be prepared by methods described herein. Methods for the preparation of enantiomers are described, for example, in Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, N.Y., 1962); and Wilen, S. H. *Tables of Resolving Agents and Optical Resolutions* p. 268 (E. L. Eliel, Ed., Univ. of Notre Dame Press, Notre Dame, Ind. 1972), each of which is hereby incorporated by reference in its entirety.

The following synthetic schemes are designed to illustrate, but not limit, general procedures for the preparation of compounds of the present invention. The reagents used can be either commercially obtained or can be prepared by standard procedures described in the literature. It is intended that the scope of this invention will cover all isomers (enantiomeric and diastereomeric) and all mixtures, including but not limited to racemic mixtures. The isomeric forms of the compounds of this invention may be separated or resolved using methods known to those skilled in the art or by synthetic methods that are stereospecific or asymmetric.

As illustrated in Scheme 1, thiazyl bromide or oxazolyl bromide (II) is coupled with aryl boronic acid in the presence of Pd(Ph₃P)₄, aqueous Na₂CO₃ in DME to produce III. Tricycle formation is accomplished by converting the carboxylic acid to the corresponding acid chloride using reagents such as SOCl₂ or (CO)₂Cl₂, conversion to the acyl azide using sodium azide which undergoes Curtius rearrangement to give the corresponding isocyanate (IV), followed by closure under heating in high boiling non-polar solvents such as dichlorobenzene. Compound (I) is then prepared by adding the amine side chain under Mannich conditions (amine, CH₂O, heating).

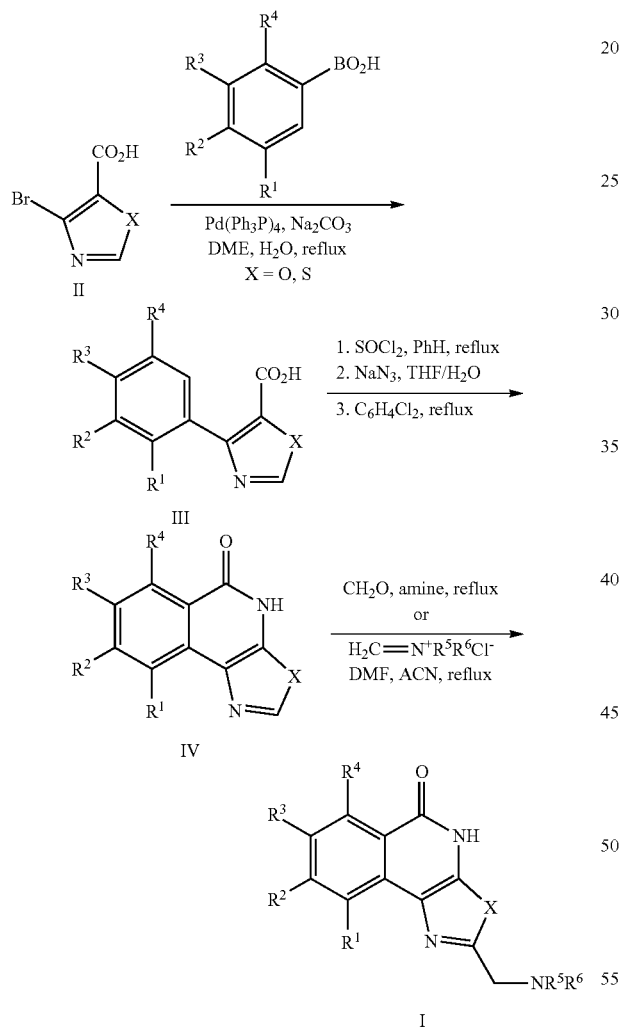

The thiazole alkyne compound (IX) can be prepared according to Scheme 2. Aminothiazole (V) was prepared according to Yamaguchi K. et al. *Bioorg. Med. Chem. Lett.* 1999, 9, 957-960. Treatment with NaNO₂, i-amyl nitrite, CH₂I₂ in acetonitrile produces the corresponding iodide (VI). Hydrolysis of the ester using conditions such as NaOH in EtOH produces the thiazole acid (VII). Conversion to the acid chloride with SOCl₂, formation of the acyl azide with NaN₃ and Curtius rearrangement/ring closure in refluxing dichlorobenzene produces VIII. Sonogashira cross-coupling using Pd(Ph₃P)₂Cl₂, CuI and 1-dimethylamino-2-propyne yields the desired thiazole alkyne (IX). Alkene analogs (X) are prepared according to Scheme 3 by combining iodo compounds (VIII) with allyl amines using standard Heck/catalytic-Pd conditions.

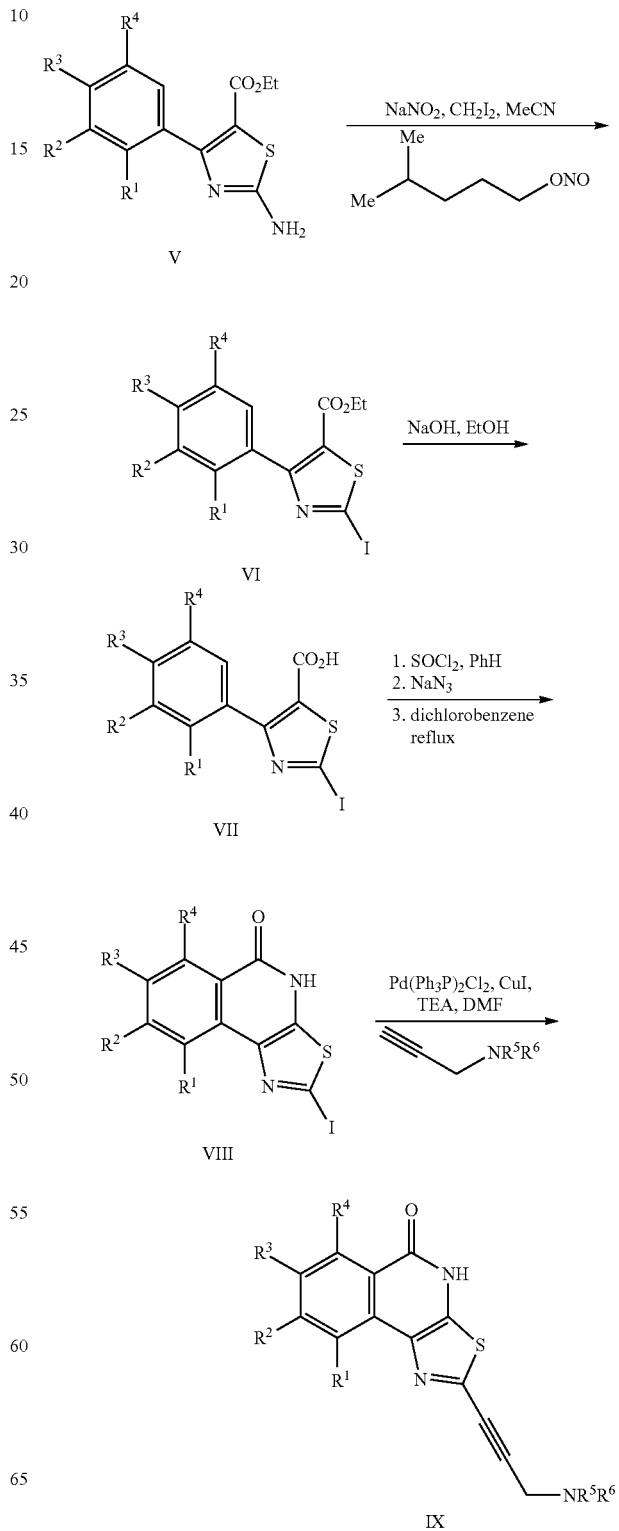

Scheme 3

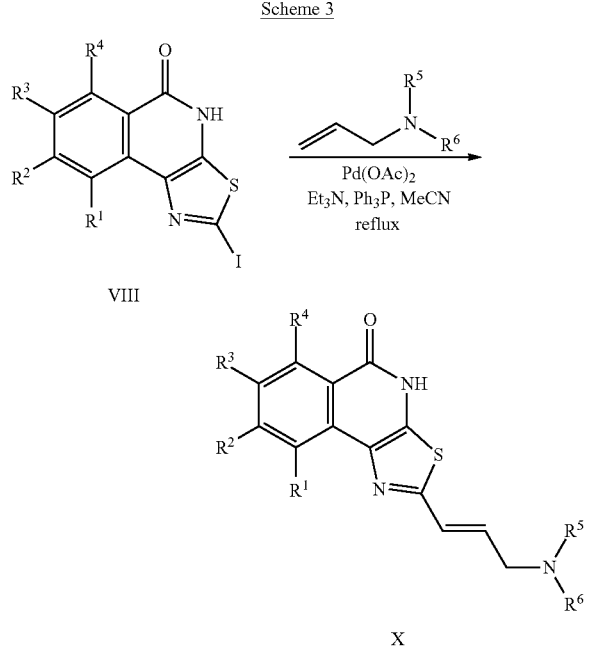

In certain embodiments, the invention relates to compositions comprising at least one compound of the present invention and one or more pharmaceutically acceptable carriers, excipients, or diluents. Such compositions are prepared in accordance with general pharmaceutical formulation procedures, such as, for example, those described in *Remington's Pharmaceutical Sciences*, 17th edition, ed. Alfonoso R. Gennaro, Mack Publishing Company, Easton, Pa. (1985), which is incorporated herein by reference in its entirety. Pharmaceutically acceptable carriers are those carriers that are compatible with the other ingredients in the formulation and are biologically acceptable.

The compounds of the present invention can be administered orally or parenterally, neat, or in combination with conventional pharmaceutical carriers. Applicable solid carriers can include one or more substances that can also act as flavoring agents, lubricants, solubilizers, suspending agents, fillers, glidants, compression aids, binders, tablet-disintegrating agents, or encapsulating materials. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers can be used in preparing solutions, suspensions, emulsions, syrups and elixirs. The active ingredient can be dissolved or suspended in a pharmaceutically acceptable liquid carrier such as water, an organic solvent, a mixture of both, or a pharmaceutically acceptable oil or fat. The liquid carrier can contain other suitable pharmaceutical additives such as, for example, solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and *arachis* oil). For parenteral administration, the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions that are sterile solutions or suspensions can be administered by, for example, intramuscular, intraperitoneal or subcutaneous injection. Sterile solutions can also be administered intravenously. Compositions for oral administration can be in either liquid or solid form.

The compounds of the present invention can be administered rectally or vaginally in the form of a conventional suppository. For administration by intranasal or intrabronchial inhalation or insufflation, the compounds of the present invention can be formulated into an aqueous or partially aqueous solution, which can then be utilized in the form of an aerosol. The compounds of the present invention can also be administered transdermally through the use of a transdermal patch containing the active compound and a carrier that is inert to the active compound, is non-toxic to the skin, and allows delivery of the agent for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the active ingredient can also be suitable. A variety of occlusive devices can be used to release the active ingredient into the blood stream such as a semipermeable membrane covering a reservoir containing the active ingredient with or without a carrier, or a matrix containing the active ingredient. Other occlusive devices are known in the literature.

Preferably the pharmaceutical composition is in unit dosage form, e.g. as tablets, capsules, powders, solutions, suspensions, emulsions, granules, or suppositories. In such form, the composition can be sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of Formula I can be provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age, and response pattern of the patient. The compounds can be administered orally, rectally, parenterally, or topically to the skin and mucosa. The usual daily dose depends on the specific compound, method of treatment and condition treated. The usual daily dose depends on the specific compound, method of treatment and condition treated. The usual daily dose is, for example, from 0.01-1000 mg/kg for oral application, preferably 0.5-500 mg/kg, either in a single dose or in subdivided doses, for example from one to three times daily and from about 0.1 to 100 mg/kg for parenteral application, preferably 0.5-50 mg/kg, from one to three times daily.

In certain embodiments, the present invention is directed to prodrugs of compounds provided herein. The term "prodrug," as used herein, means a compound that is convertible in vivo by metabolic means (e.g. by hydrolysis) to a compound of Formula I. Various forms of prodrugs are known in the art such as those discussed in, for example, Bundgaard, (ed.), *Design of Prodrugs*, Elsevier (1985); Widder, et al. (ed.), *Methods in Enzymology*, vol. 4, Academic Press (1985); Krogsgaard-Larsen, et al., (ed). "*Design and Application of Prodrugs, Textbook of Drug Design and Development*, Chapter 5, 113-191 (1991), Bundgaard, et al., *Journal of Drug Delivery Reviews*, 8:1-38(1992), Bundgaard, *J. of Pharmaceutical Sciences*, 77:285 et seq. (1988); and Higuchi and Stella (eds.) *Prodrugs as Novel Drug Delivery Systems*, American Chemical Society (1975), each of which is hereby incorporated by reference in its entirety.

EXAMPLES

The following examples are illustrative of certain embodiments of the invention and should not be considered to limit the scope of the invention. The reagents used can be either commercially obtained or can be prepared by standard procedures described in the literature. It is intended that the scope of this invention will cover all isomers (enantiomeric and diastereomeric) and all mixtures, including but not limited to racemic mixtures. The isomeric forms of the compounds of this invention may be separated or resolved using methods known to those skilled in the art or by synthetic methods that are stereospecific or asymmetric.

Example 1

2-[(Dimethylamino)methyl][1,3]thiazolo[5,4-c]isoquinolin-5(4H)-one hydrochloride

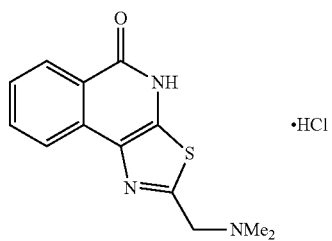 [SMILES: CN(C)Cc1nc2c([nH]c(=O)c3ccccc32)s1 ; Cl]

Step 1

4-Phenyl-1,3-thiazole-5-carboxylic acid

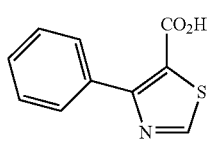

Ethyl 4-phenyl-1,3-thiazole-5-carboxylate, prepared according to known procedure (Yamaguchi K. et al. *Biorg. Med. Chem. Lett.* 1999, 9(7), 957-960) (0.28 g, 1.2 mmol), was dissolved with 96% ethanol (10 ml) and was treated with sodium hydroxide (0.4 g) and stirred under reflux for 16 hours. The solution was acidified with 3N HCl solution, and extracted with ethyl acetate (5×50 ml). The organic layers were collected, dried (over $Na_2SO_4$) and evaporated under vacuum thus obtaining 33 (72% yield) as pure solid, mp: 204-205° C.

mp: 204-205° C.
$^1$H-NMR (DMSO, 200 MHz): δ 7.38-7.42 (m, 3H, Ph), 7.67-7.73 (m, 2H, Ph), 8.28 (s, 1H, H-Tz).

Step 2

1,3-Thiazolo[5,4-c]isoquinolin-5(4H)-one

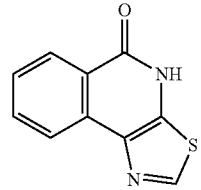 [SMILES: O=c1[nH]c2scnc2c2ccccc12]

Thionyl chloride (1 ml) was added to a suspension of 4-phenyl-1,3-thiazole-5-carboxylic acid (300 mg, 1.46 mmol) in 10 ml of dry benzene and the mixture was refluxed for 2 hours. The solvent and the excess of thionyl chloride were removed under reduced pressure; the residue was taken up using 10 ml of dry THF and cooled to 0° C. Sodium azide (1.5 mmol) dissolved in the minimal amount of water was quickly added and the resulting solution was stirred for 1 hour at room temperature. After pouring into 100 ml of cracked ice/$H_2O$ and extraction with diethyl ether (4×100 ml), the collected organic layers were dried over $Na_2SO_4$. The filtrate was gently evaporated under reduced pressure, the residue was dissolved in 10 ml of o-dichlorobenzene, and the resulting mixture was refluxed for 5-10 hours. The mixture was then cooled, and directly submitted to flash chromatography, elution with dichloromethane/methanol (99/1) afforded to the title compound.

Yield: 20%.
mp>200° C.
$^1$H NMR: (DMSO, 400 MHz) δ: 7.58 (t, J=8.1 Hz, 1H, H-Ph), 7.85 (t, J=7.9 Hz, 1H, H-Ph), 8.24 (d, J=3 Hz, 1H, H-Ph); 8.26 (d, J=3.2 Hz, 1H, H-Ph), 8.91 (s, H, H-Tz) 12.39 (s, H, NH).

Step 3

2-[(Dimethylamino)methyl]-8-methoxythieno[2,3-c]isoquinolin-5(4H)-one hydrochloride

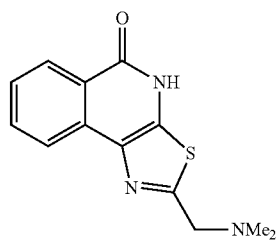 [SMILES: CN(C)Cc1nc2c([nH]c(=O)c3ccccc32)s1]

1,3-Thiazolo[5,4-c]isoquinolin-5(4H)-one (55 mg, 0.27 mmol) was dissolved in a mixture of dry dimethylformamide (1 ml) and dry acetonitrile (2 ml) and treated with N,N-dimethyl(methylene)ammonium chloride (1 mmol) prepared according to known procedure (Kinast G. et al. *Angew. Chem. Int. Ed. Engl.* 1976, 15(4), 239-240; Bohme H. et al. *Chem. Ber.* 1960, 93, 1305). The reaction mixture was refluxed overnight, and the resulting precipitate was filtered and washed with dry diethyl ether to give the title compound. Yield: 55%.

mp>200° C.

$^1$H NMR: (CD$_3$OD, 400 MHz) δ: 2.39 (s, 6H, N(CH$_3$)$_2$), 3.35 (s, 2H, CH$_2$N), 7.50 (t, J=8.2 Hz, 1H, H-Ph), 7.76 (t, J=8.4 Hz, 1H, H-Ph), 8.24 (d, J=7.5 Hz, 1H, H-Ph), 8.34 (d, J=8.1 Hz, 1H, H-Tz); $^{13}$C NMR: (CD$_3$OD, 100.6 MHz) δ: 45.19, 60.62, 122.25, 123.72, 126.73, 133.10, 133.32, 135.91, 161.92, 162.75.

Example 2

2-[3-(Dimethylamino)prop-1-yn-1-yl][1,3]thiazolo[5,4-c]isoquinolin-5(4H)-one

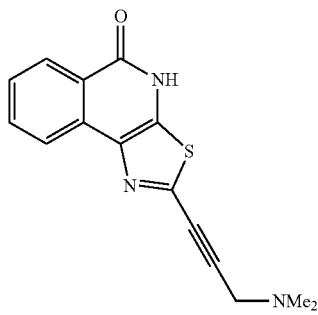 [SMILES: CN(C)CC#Cc1nc2c([nH]c(=O)c3ccccc32)s1]

Step 1

Ethyl 2-iodo-4-phenyl-1,3-thiazole-5-carboxylate

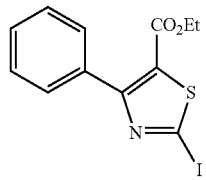 [SMILES: CCOC(=O)c1sc(I)nc1-c1ccccc1]

Ethyl 2-amino-4-phenyl-1,3-thiazole-5-carboxylate (6.1 g, 25 mmol), prepared according to known procedure (Yamaguchi K. et al. *Biorg. Med. Chem. Lett.* 1999, 9(7), 957-960), was dissolved in MeCN (240 ml) and treated with CH$_2$I$_2$ (7 ml, 150 mmol) isoamylnitrite (12 ml, 112.5 mmol). The reaction was stirred at room temperature for 1 hour. The solvents were removed under high vacuum and the mixture was submitted to flash chromatography by eluting with light petroleum/ethyl acetate (9:1) to give the title compound as a solid. Yield: 57%.

mp: 104-106° C.

$^1$H-NMR (CDCl$_3$, 200 MHz): δ 1.38 (t J=7.10 Hz, 3H, CH$_3$), 4.37 (q J=7.13 Hz, 2H, CH$_2$), 7.50-7.55 (m, 3H, Ph), 7.80-7.86 (m, 2H, Ph).

Step 2

2-Iodo-4-phenyl-1,3-thiazole-5-carboxylic acid

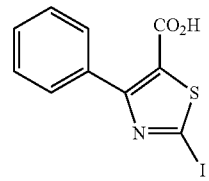 [SMILES: O=C(O)c1sc(I)nc1-c1ccccc1]

Ethyl 2-iodo-4-phenyl-1,3-thiazole-5-carboxylate (5 g, 13.9 mmol) was dissolved in 96% ethanol (30 ml), treated with solid sodium hydroxide (1.1 g) and stirred at room temperature for 1 hour. The solution was acidified with 3 N HCl solution, and extracted with ethyl acetate (5×50 ml). The organic layers were combined, dried over Na$_2$SO$_4$ and evaporated to give the title compound as a solid. Yield: 92% yield.

mp: 194-196° C.

$^1$H-NMR (CDCl$_3$, 200 MHz): δ 7.41-7.48 (m, 3H, Ph), 7.97-8.01 (m, 2H, Ph).

Step 3

2-Iodo-1,3-thiazolo[5,4-c]isoquinolin-5(4H)-one

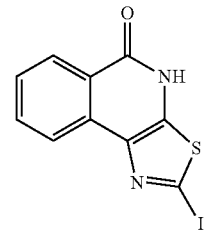 [SMILES: O=c1[nH]c2sc(I)nc2c2ccccc12]

Thionyl chloride (1 ml) was added to a suspension of 2-iodo-4-phenyl-1,3-thiazole-5-carboxylic acid (2.2 g, 6.6 mmol) in 30 ml of dry benzene and the mixture was refluxed for 2 hours. The solvent and the excess of thionyl chloride were removed under reduced pressure, the residue was taken up using 20 ml of dry THF, cooled to 0° C. and NaN$_3$ (10 mmol) dissolved in the minimal amount of water was quickly added. After stirring for h at room temperature, the reaction mixture was poured into 100 ml of cracked ice/water, extracted with diethyl ether (5×100 ml), and the combined organics were dried over Na$_2$SO$_4$. After filtration, the filtrate was gently evaporated under reduced pressure and the residue was dissolved in 20 ml of o-dichlorobenzene and refluxed for 5 hours. The mixture was then cooled, and directly chromatographed on SiO$_2$ gel, eluting with dichloromethane/methanol (99/1), to produce the title compound as a solid. Yield: 23% yield.

mp: >250° C.

¹H-NMR (DMSO, 200 MHz) δ 7.69 (t J=7.81 Hz, 1H, H-Ph), 7.96 (t J=7.90 Hz, 1H, H-Ph), 8.21 (d J=8.20 Hz, 1H, Ph), 8.34 (d J=7.81 Hz, 1H, Ph), 12.38 (s, 1H, CONH).

Step 4

2-[3-(Dimethylamino)prop-1-yn-1-yl]-1,3-thiazolo[5,4-c]isoquinolin-5(4H)-one (5)

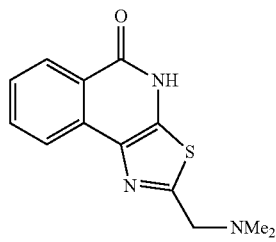 [SMILES: CN(C)Cc1nc2c([nH]c(=O)c3ccccc32)s1]

2-Iodo-1,3-thiazolo[5,4-c]isoquinolin-5(4H)-one (0.1 g, 0.3 mmol), DMF (10 ml), 1-dimethylamino-2-propyne (0.25 g, 3.05 mmol), (Ph₃P)₂PdCl₂ (10 mg), CuI (1 mg), and triethylamine (1.2 ml) were stirred at room temperature for 4 hours. The solvent was removed under reduced pressure and the mixture was chromatographed on SiO₂ gel, eluting, with dichloromethane/methanol (98/2), to produce the title compound. Yield: 68% yield.

mp: 216-221° C. dec.

¹H-NMR (DMSO, 400 MHz) δ 2.65 (s, 6H, N(CH₃)₂), 3.60 (s, 2H, CH₂N), 7.60 (t J=7.58 Hz, 1H, H-Ph), 7.86 (t J=7.23 Hz, 1H, H-Ph), 8.19-8.26 (m, 2H, H-Ph), 12.36 (s, 1H, CONH).

¹³C NMR: (DMSO, 100.6 MHz) δ: 45.65, 49.50, 80.13, 94.02, 124.26, 125.93, 129.27, 129.75, 134.00, 134.24, 135.37, 138.86, 139.64, 162.81.

Example 3

2-(2-(Dimethylamino)ethyl)thiazolo[5,4-c]isoquinolin-5(4H)-one

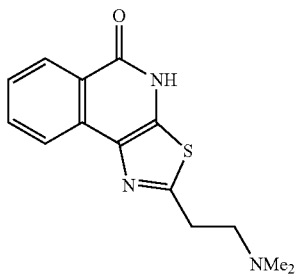 [SMILES: CN(C)CCc1nc2c([nH]c(=O)c3ccccc32)s1]

2-(2-(Dimethylamino)ethyl)thiazolo[5,4-c]isoquinolin-5(4H)-one was prepared from intermediate VIII in Scheme 2.

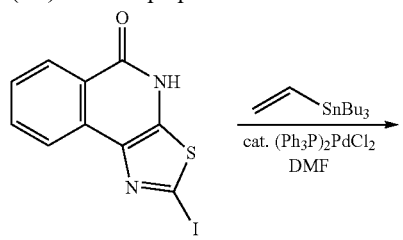

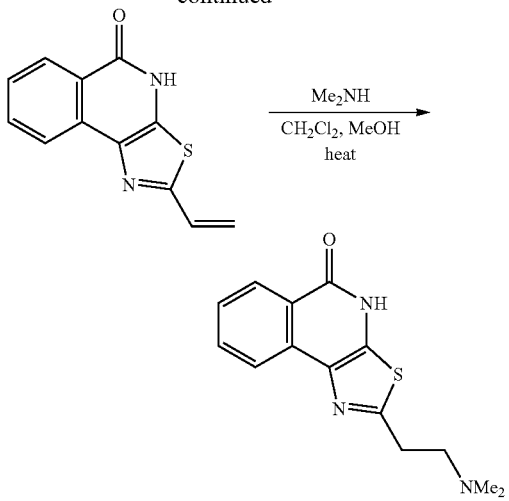

Step 1

2-Vinyl-4H-1,3-thiazolo[5,4-c]isoquinolin-5-one

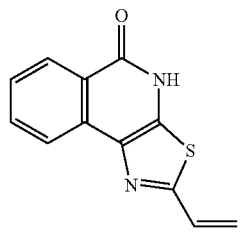 [SMILES: C=Cc1nc2c([nH]c(=O)c3ccccc32)s1]

Bis(triphenylphosphine)palladium dichloride (0.005 g, 0.007 mmol) was added to a solution of 2-iodo-4H-1,3-thiazolo[5,4-c]isoquinolin-5-one (0.115 g, 0.35 mmol) and DMF (5 ml) at 23° C. After 30 minutes, tributylvinylstannane (0.11 ml, 0.37 mmol) was added, and the reaction mixture was stirred overnight at 45° C. All volatiles were evaporated, and the resulting oil was purified by flash-chromatography (CH₂Cl₂/methanol, 99/1) to afford the title compound as a yellow solid (a quantitative yield). m.p 235-239° C. (dec.); ¹H NMR (200 MHz, DMSO) δ 5.55 (d, 1H, CHH, J=11 Hz), 5.95 (d, 1H, CHH, J=17 Hz), 6.85-7.00 (m, 1H, CH), 7.47-7.54 (m, 1H, Ar), 7.74-7.82 (m, 1H, Ar), 8.09-8.20 (m, 2H, Ar), 12.43 (bs, 1H, NH).

Step 2

2-(2-Dimethylamino-ethyl)-4H-1,3-thiazolo[5,4-c]isoquinolin-5-one (3)

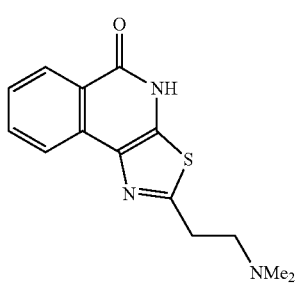 [SMILES: CN(C)CCc1nc2c([nH]c(=O)c3ccccc32)s1]

To a suspension of 2-vinyl-4H-1,3-thiazolo[5,4-c]isoquinolin-5-one (0.05 g, 0.22 mmol) and CH₂Cl₂/methanol (6 ml; 1/1) was added dimethylamine (0.33 ml of 2M solution in THF, 0.66 mmol). After stirring at 65° C. for 48 hours, the reaction mixture was concentrated under reduced pressure and purified by flash-chromatography (CH₂Cl₂/methanol, 90/10). Recrystallization from methanol/diethyl ether yielded 0.038 g (a 63% yield) of the title compound as a white solid. m.p. 236-240° C. (dec.); $^1$H NMR (400 MHz, DMSO) δ 2.85 (s, 6H, (CH₂)₂N(CH₃)₂), 3.52-3.56 (m, 4H, (CH₂)₂N (CH₃)₂), 7.56-7.59 (m, 1H, Ar), 7.84-7.87 (m, 1H, Ar), 8.19-8.26 (m, 2H, Ar), 12.37 (bs, NH); $^{13}$C NMR (100.6 MHz, DMSO) δ 29.71, 44.26, 56.79, 124.03, 125.74, 128.69, 129.79, 133.45, 134.44, 135.15, 158.51, 162.72.

Example 4

2-((Dimethylamino)methyl)-9-hydroxythiazolo[5,4-c]isoquinolin-5(4H)-one

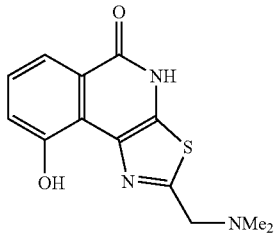 [SMILES: CN(C)Cc1nc2c([nH]c(=O)c3cccc(O)c32)s1]

2-((Dimethylamino)methyl)-9-hydroxythiazolo[5,4-c]isoquinolin-5(4H)-one was prepared as shown below.

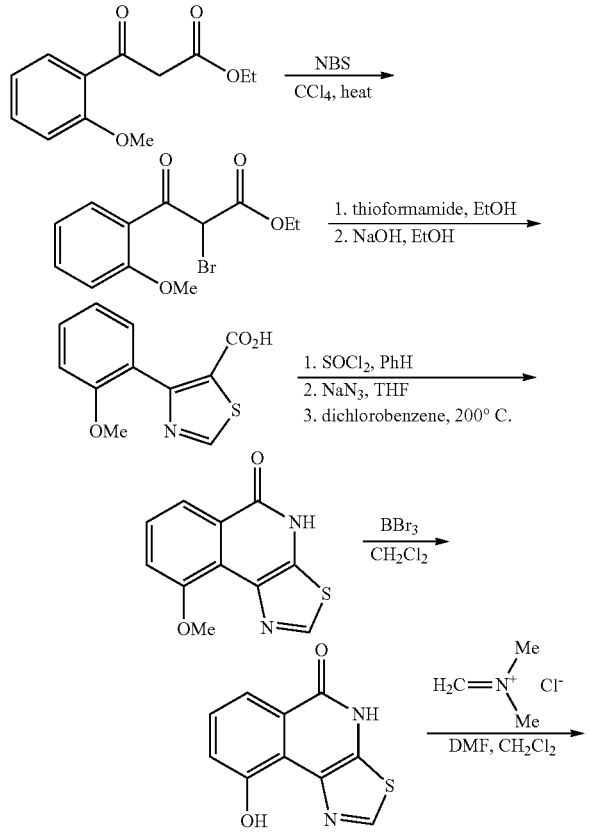

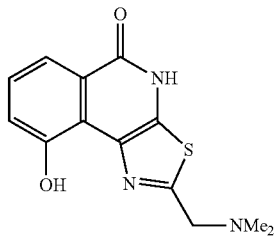

Step 1

2-Bromo-3-(2-methoxyphenyl)-3-oxo-propionic acid ethyl ester

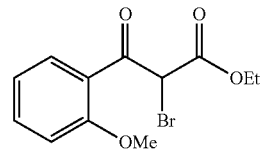 [SMILES: CCOC(=O)C(Br)C(=O)c1ccccc1OC]

To a solution of 3-(2-methoxy-phenyl)-3-oxo-propionic acid ethyl ester (5.3 g, 23.9 mmol; prepared as reported in *J. Org. Chem.* 2001, 66, 6323-6332) in carbon tetrachloride (50 ml) was added of N-bromosuccinimide (5.1 g, 28.7 mmol) portion-wise The reaction mixture was stirred at room temperature under an Ar atmosphere for 4 hours. Water was added, the resulting mixture was extracted with CHCl₃, and the organics were dried over Na₂SO₄ and evaporated under reduced pressure to yield the title compound as a yellow oil. $^1$H NMR (200 MHz, CDCl₃) δ 1.25 (t, 3H, COOCH₂CH₃, J=7), 3.92 (s, 3H, OCH₃), 4.25 (q, 2H, COOCH₂CH₃, J=6.4), 5.82 (s, 1H, CHBr), 6.97-7.11 (m, 2H, Ar), 7.51-7.60 (m, 1H, Ar), 7.90-7.95 (m, 1H, Ar).

Step 2

4-(2-Methoxyphenyl)-thiazole-5-carboxylic acid

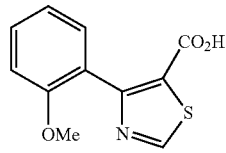 [SMILES: COc1ccccc1-c1ncsc1C(=O)O]

To a 0° C. solution of thioformamide (prepared according to *Eur. J. Med. Chem.* 2004, 39, 867-872) (0.70 g, 11.5 mmol) in absolute EtOH (1 ml) was added a solution of 2-bromo-3-(2-methoxyphenyl)-3-oxo-propionic acid ethyl ester (2.4 g, 7.97 mmol) in ethanol abs. (9 ml) in drops. The reaction mixture was stirred at room temperature for 72 hours. After quenching with water and extraction with chloroform, the organics were dried over Na₂SO₄ and evaporated. Flash chromatography on SiO₂ gel (petroleum ether/ethyl acetate, 60/40) gave crude 4-(2-methoxy-phenyl)-thiazole-5-carboxylic acid ethyl ester that was used in the next step without further purification.

To the crude 4-(2-methoxy-phenyl)-thiazole-5-carboxylic acid ethyl ester (0.88 g) in 95% ethanol (20 ml) was added sodium hydroxide (0.67 g, 16.75 mmol) and the resulting mixture was stirred at room temperature for 5 hours. After acidification with 3N HCl and concentration under vacuum, the remaining residue was taken up with water, and extracted with ethyl acetate (3×50 ml). The combined organics were dried over Na$_2$SO$_4$ and evaporated under reduced pressure to afford the title compound as a yellow solid (0.77 g, 3.28 mmol, a 41% yield). m.p.: 170-172° C.; $^1$H NMR (200 MHz, DMSO) δ 3.72 (s, 3H, OCH$_3$), 6.99-7.12 (m, 2H, Ar), 7.35-7.46 (m, 2H, Ar), 9.26 (s, 1H, 2-CH).

Step 3

9-Methoxy-4H-1,3-thiazolo[5,4-c]isoquinolin-5-one

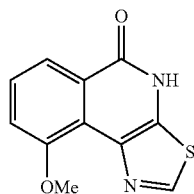 [SMILES: COc1cccc2c(=O)[nH]c3scnc3c12]

To a suspension of 4-(2-methoxyphenyl)-thiazole-5-carboxylic acid (0.56 g, 2.38 mmol) and benzene (10 ml), was added thionyl chloride (0.42 g, 3.57 mmol), and the reaction mixture was refluxed for 5 h. All volatiles were evaporated, and the resulting yellow oil was taken up in dry THF (10 ml), cooled to 0° C., and solution of sodium azide (0.186 g, 2.86 mmol) in water (1 ml) was added. The reaction mixture was stirred at 0° C. for 30 minutes and at room temperature for 3 hours. After quenching with water, the mixture was extracted with diethyl ether, dried over sodium sulfate and carefully evaporated under reduced pressure (rotovap water temperature kept below 25° C.). The resulting solid was dissolved in 1,2-dichlorobenzene (10 ml) and heated at 200° C. for 5 h. After cooling the evaporation of all volatiles, the resulting material was purified by flash-chromatography on SiO$_2$ (CH$_2$Cl$_2$/methanol, 94/6) to yield the title compound (0.120 g, 0.51 mmol, a 22% yield) as a solid; m.p.: 220-222° C. (dec.); $^1$H NMR (200 MHz, DMSO) δ 3.94 (s, 3H, OCH$_3$), 7.36-7.62 (m, 2H, Ar), 7.87 (d, 1H, Ar), 8.86 (s, 1H, 2-CH), 12.58 (s, 1H, NH).

Step 4

9-Hydroxy-4H-1,3-thiazolo[5,4-c]isoquinolin-5-one

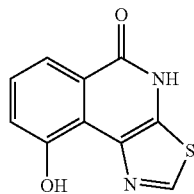 [SMILES: O=c1[nH]c2scnc2c2c(O)cccc12]

To a suspension of 9-methoxy-4H-1,3-thiazolo[5,4-c]isoquinolin-5-one (0.048 g, 0.21 mmol) and CH$_2$Cl$_2$ (2 ml) was added boron tribromide (1.05 ml of 1M sol. in CH$_2$Cl$_2$, 1.05 mmol), and the resulting mixture was stirred at room temperature overnight. The reaction mixture was evaporated, methanol (2 ml) was added, the resulting mixture stirred for 1 hour and then evaporated. The resulting solid was purified by flash chromatography on SiO$_2$ gel to yield the title compound (0.042 g, a 90% yield) as a solid. m.p.>250° C.; $^1$H NMR (400 MHz, DMSO) δ 7.28 (d, 1H, Ar), 7.47 (t, 1H, Ar), 7.75 (d, 1H, Ar), 9.06 (s, 1H, 2-CH), 10.36 (s, 1H, OH), 12.41 (s, 1H, NH).

Step 5

2-Dimethylaminomethyl-9-hydroxy-4H-1,3-thiazolo[5,4-c]isoquinolin-5-one hydrochloride

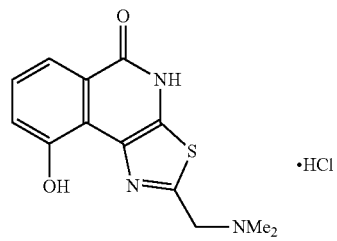 [SMILES: CN(C)Cc1nc2c([nH]c(=O)c3cccc(O)c32)s1 ; Cl]

To a solution of 9-hydroxy-4H-1,3-thiazolo[5,4-c]isoquinolin-5-one in DMF/acetonitrile (3 ml, 1:2) was added dimethyl-methylene-ammonium chloride (0.043 g, 0.46 mmol) and the resulting mixture was refluxed under Ar for 42 hours. After cooling and concentration, the residue was purified via flash chromatography on SiO$_2$ to give the title compound (0.008 g, a 13% yield) as solid. m.p.>250° C.; $^1$H NMR (400 MHz, DMSO) δ 2.36 (s, 6H, N(CH$_3$)$_2$), 3.93 (m, 2H, CH$_2$N), 7.24 (d, 1H, Ar), 7.44 (t, 1H, Ar), 7.74 (d, 1H, Ar), 10.23 (s, 1H, OH), 12.30 (s, 1H, NH); $^{13}$C NMR (100.6 MHz, DMSO) δ 46.83, 61.38, 119.94, 120.56, 121.00, 126.83, 129.95, 131.75, 137.39, 154.41, 162.54.

Example 5

9-Hydroxy-2-(morpholin-4-ylmethyl)[1,3]thiazolo[5,4-c]isoquinolin-5(4H)-one

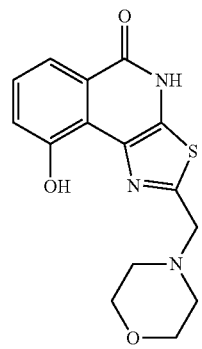 [SMILES: O=c1[nH]c2sc(CN3CCOCC3)nc2c2c(O)cccc12]

Step 1

9-Methoxy-2-(morpholinomethyl)thiazolo[5,4-c]isoquinolin-5(4H)-one

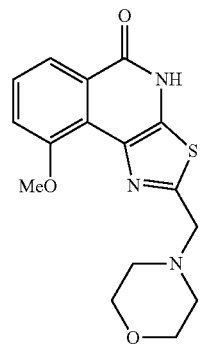 [SMILES: COc1cccc2c(=O)[nH]c3sc(CN4CCOCC4)nc3c12]

Morpholine (950 μL, 0.011 mmol) was added slowly to solution of 9-methoxythiazolo[5,4-c]isoquinolin-5(4H)-one in 2.6 mL of 37% aqueous formaldehyde and the resulting reaction mixture was refluxed for 7 hours. The reaction was monitored by TLC until all starting material was consumed. After cooling to room temperature, the reaction mixture was partitioned between water and ethyl acetate, the organics were separated, washed with brine, dried over Na$_2$SO$_4$ and solvent was evaporated under reduced pressure to produce the title compound as a pale solid.

MS (ES$^+$) m/z 332 (M+H).

Step 2

9-Hydroxy-2-(morpholin-4-ylmethyl)[1,3]thiazolo[5,4-c]isoquinolin-5(4H)-one

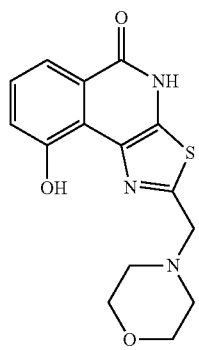 [SMILES: O=c1[nH]c2sc(CN3CCOCC3)nc2c2c(O)cccc12]

The title compound was prepared according to the procedure of Example 4, Step 4, using the product of Step 1 above as the starting material.

MS (ES$^+$) m/z 318 (M+H).

Example 6

9-Hydroxy-2-(piperidin-1-ylmethyl)[1,3]thiazolo[5,4-c]isoquinolin-5(4H)-one

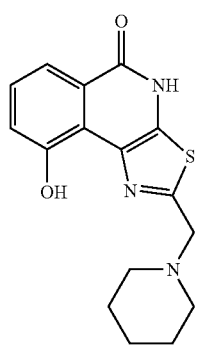 [SMILES: O=c1[nH]c2sc(CN3CCCCC3)nc2c2c(O)cccc12]

Step 1

9-Methoxy-2-(piperidin-1-ylmethyl)thiazolo[5,4-c]isoquinolin-5(4H)-one

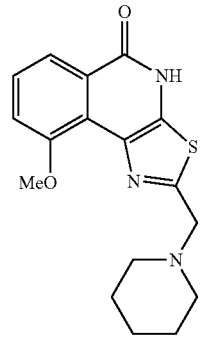 [SMILES: COc1cccc2c(=O)[nH]c3sc(CN4CCCCC4)nc3c12]

The title compound was prepared according to the procedure of Example 5, Step 1 above except that piperidine was used in place of morpholine.

MS (ES$^+$) m/z 330 (M+H).

Step 2

9-Hydroxy-2-(piperidin-1-ylmethyl)[1,3]thiazolo[5,4-c]isoquinolin-5(4H)-one

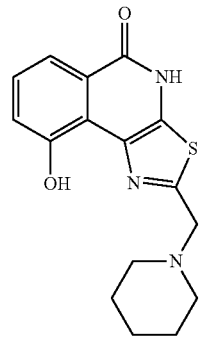 [SMILES: O=c1[nH]c2sc(CN3CCCCC3)nc2c2c(O)cccc12]

The title compound was prepared according to the procedure of Example 5, Step 2 using the product of Step 1 above as the starting material.

MS (ES$^+$) m/z 316 (M+H).

Example 7

9-Hydroxy-2-(pyrrolidin-1-ylmethyl)[1,3]thiazolo[5,4-c]isoquinolin-5(4H)-one

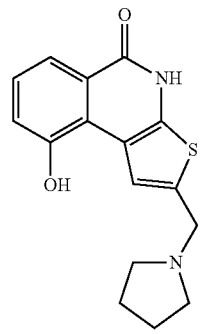 [SMILES: O=c1[nH]c2sc(CN3CCCC3)cc2c2c(O)cccc12]

Step 1

9-Methoxy-2-(pyrrolidin-1-ylmethyl)thiazolo[5,4-c]isoquinolin-5(4H)-one

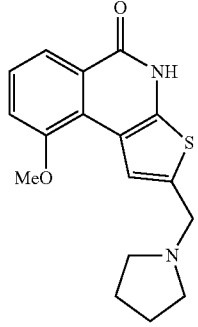 [SMILES: COc1cccc2c(=O)[nH]c3sc(CN4CCCC4)cc3c12]

The title compound was prepared according to the procedure of Example 5, Step 1 above except that pyrrolidine was used in place of morpholine.
MS (ES$^+$) m/z 316 (M+H).

Step 2

9-Hydroxy-2-(pyrrolidin-1-ylmethyl)[1,3]thiazolo[5,4-c]isoquinolin-5(4H)-one

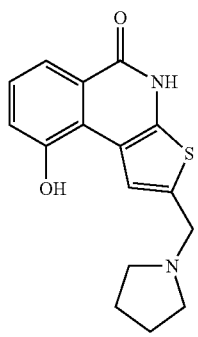 [SMILES: O=c1[nH]c2sc(CN3CCCC3)cc2c2c(O)cccc12]

The title compound was prepared according to the procedure of Example 4, Step 4 using the product of Step 1 above as the starting material.
MS (ES$^+$) m/z 302 (M+H).

Example 8

2-{[(3R)-3-(dimethylamino)pyrrolidin-1-yl]methyl}-9-hydroxy[1,3]thiazolo[5,4-c]isoquinolin-5(4H)-one

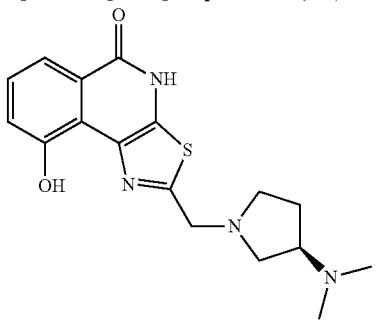

Step 1

(R)-2-((3-(dimethylamino)pyrrolidin-1-yl)methyl)-9-methoxythiazolo[5,4-c]isoquinolin-5(4H)-one

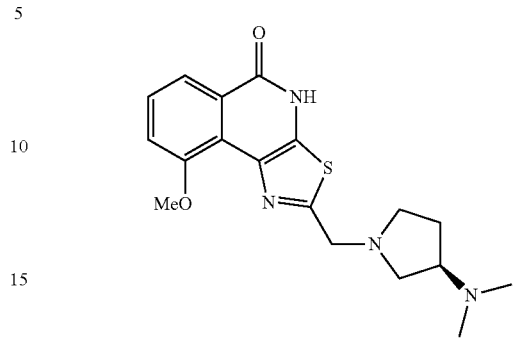

The title compound was prepared according to the procedure of Example 5, Step 1 above except that (R)—N,N-dimethylpyrrolidin-3-amine was used in place of morpholine.
MS (ES$^+$) m/z 359 (M+H).

Step 2

2-{[(3R)-3-(dimethylamino)pyrrolidin-1-yl]methyl}-9-hydroxy[1,3]thiazolo[5,4-c]isoquinolin-5(4H)-one

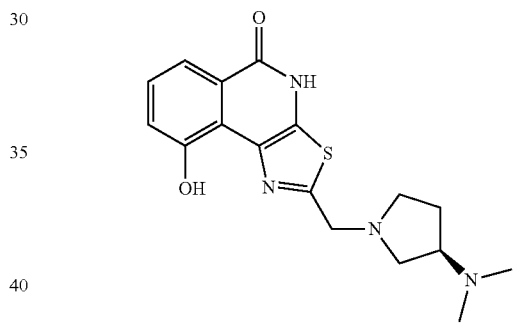

The title compound was prepared according to the procedure of Example 4, Step 4 using the product of Step 1 above as the starting material.
MS (ES$^+$) m/z 345 (M+H).

Example 9

9-Hydroxy-2-(octahydroquinolin-1(2H)-ylmethyl)[1,3]thiazolo[5,4-c]isoquinolin-5(4H)-one

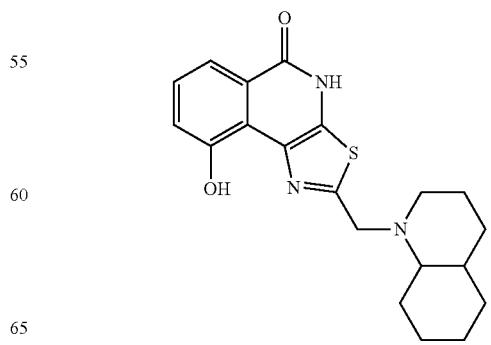

Step 1

9-Methoxy-2-((octahydroquinolin-1(2H)-yl)methyl)thiazolo[5,4-c]isoquinolin-5(4H)-one

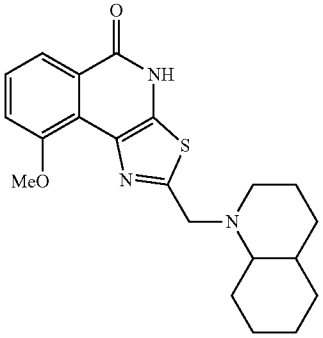 [SMILES: COc1cccc2c(=O)[nH]c3sc(CN4CCCC5CCCCC54)nc3c12]

The title compound was prepared according to the procedure of Example 5, Step 1 above except that decahydroquinoline was used in place of morpholine.
MS (ES+) m/z 384 (M+H).

Step 2

9-Hydroxy-2-(octahydroquinolin-1(2H)-ylmethyl)[1,3]thiazolo[5,4-c]isoquinolin-5(4H)-one

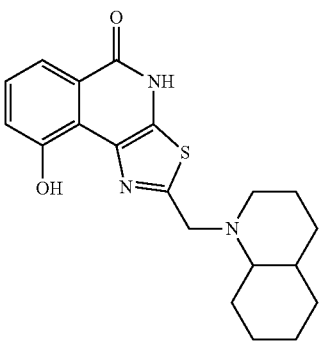 [SMILES: O=c1[nH]c2sc(CN3CCCC4CCCCC43)nc2c2c(O)cccc12]

The title compound was prepared according to the procedure of Example 4, Step 4 using the product of Step 1 above as the starting material.
MS (ES+) m/z 370 (M+H).

Example 10

2-{[(2R,6S)-2,6-Dimethylmorpholin-4-yl]methyl}-9-hydroxy[1,3]thiazolo[5,4-c]isoquinolin-5(4H)-one

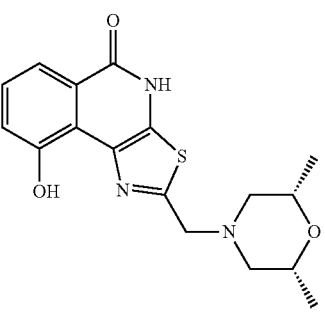 [SMILES: C[C@@H]1CN(Cc2nc3c([nH]c(=O)c4cccc(O)c43)s2)C[C@H](C)O1]

Step 1

2-(((2R,6S)-2,6-Dimethylmorpholino)methyl)-9-methoxythiazolo[5,4-c]isoquinolin-5(4H)-one

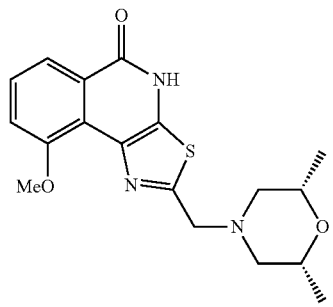 [SMILES: COc1cccc2c(=O)[nH]c3sc(CN4C[C@@H](C)O[C@@H](C)C4)nc3c12]

The title compound was prepared according to the procedure of Example 5, Step 1 above except that (2R,6S)-2,6-dimethylmorpholine was used in place of morpholine.
MS (ES+) m/z 360 (M+H).

Step 2

2-{[(2R,6S)-2,6-Dimethylmorpholin-4-yl]methyl}-9-hydroxy[1,3]thiazolo[5,4-c]isoquinolin-5(4H)-one

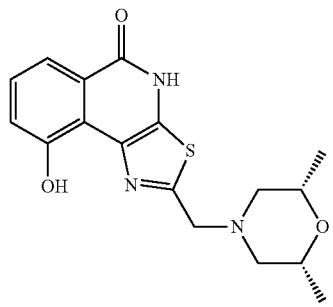 [SMILES: C[C@@H]1CN(Cc2nc3c([nH]c(=O)c4cccc(O)c43)s2)C[C@H](C)O1]

The title compound was prepared according to the procedure of Example 4, Step 4 using the product of Step 1 above as the starting material.
MS (ES+) m/z 346 (M+H).

Example 11

9-Hydroxy-2-[(2-methylpyrrolidin-1-yl)methyl][1,3]thiazolo[5,4-c]isoquinolin-5(4H)-one

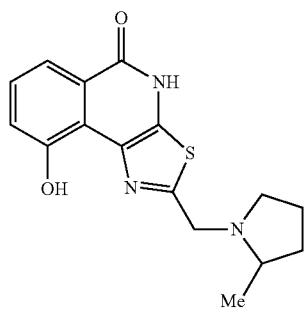 [SMILES: CC1CCCN1Cc1nc2c([nH]c(=O)c3cccc(O)c32)s1]

Step 1

9-Methoxy-2-((2-methyl pyrrolidin-1-yl)methyl)thiazolo[5,4-c]isoquinolin-5(4H)-one

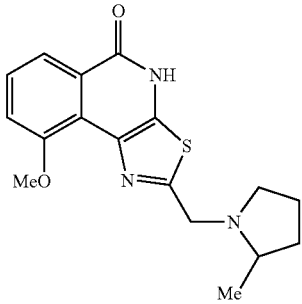 [SMILES: COc1cccc2c(=O)[nH]c3sc(CN4CCCC4C)nc3c12]

The title compound was prepared according to Example 5 Step 1 above except that dibenzylamine was used in place of morpholine.
MS (ES$^+$) m/z 330 (M+H).

Step 2

9-Hydroxy-2-[(2-methylpyrrolidin-1-yl)methyl][1,3]thiazolo[5,4-c]isoquinolin-5(4H)-one

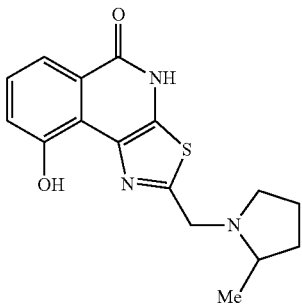 [SMILES: CC1CCCN1Cc1nc2c([nH]c(=O)c3cccc(O)c32)s1]

The title compound was prepared according to the procedure of Example 4, Step 4 using the product of Step 1 above as the starting material.
MS (ES$^+$) m/z 316 (M+H).

Example 12

9-Hydroxy-2-{[(2R)-2-(trifluoromethyl)pyrrolidin-1-yl]methyl}[1,3]thiazolo[5,4-c]isoquinolin-5(4H)-one

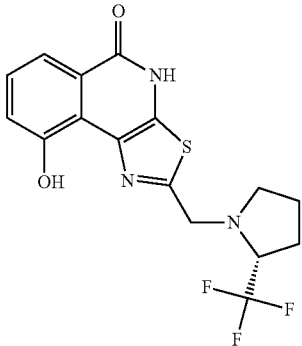 [SMILES: O=c1[nH]c2sc(CN3CCC[C@@H]3C(F)(F)F)nc2c2c(O)cccc12]

Step 1

(R)-9-methoxy-2-((2-(trifluoromethyl)pyrrolidin-1-yl)methyl)thiazolo[5,4-c]isoquinolin-5(4H)-one

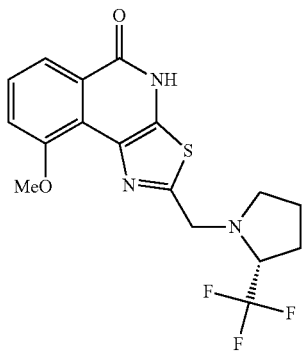 [SMILES: COc1cccc2c(=O)[nH]c3sc(CN4CCC[C@@H]4C(F)(F)F)nc3c12]

The title compound was prepared according to the procedure of Example 5, Step 1 above except that (R)-2-(trifluoromethyl)pyrrolidine was used in place of morpholine.
MS (ES$^+$) m/z 384 (M+H).

Step 2

9-Hydroxy-2-{[(2R)-2-(trifluoromethyl)pyrrolidin-1-yl]methyl}[1,3]thiazolo[5,4-c]isoquinolin-5(4H)-one

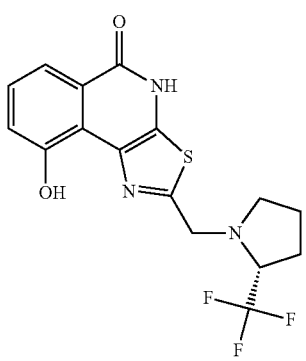 [SMILES: O=c1[nH]c2sc(CN3CCC[C@@H]3C(F)(F)F)nc2c2c(O)cccc12]

The title compound was prepared according to the procedure of Example 4, Step 4 using the product of Step 1 above as the starting material.
MS (ES$^+$) m/z 370 (M+H).

Example 13

2-{[(2R,6S)-2,6-Dimethylpiperidin-1-yl]methyl}-9-hydroxy[1,3]thiazolo[5,4-c]isoquinolin-5(4H)-one

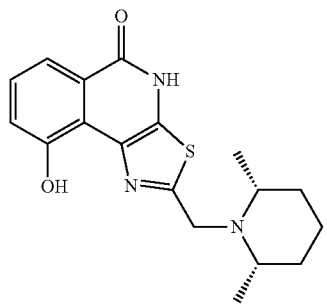 [SMILES: C[C@@H]1CCC[C@H](C)N1Cc1nc2c([nH]c(=O)c3cccc(O)c32)s1]

Step 1

2-(((2S,6R)-2,6-dimethylpiperidin-1-yl)methyl)-9-methoxythiazolo[5,4-c]isoquinolin-5(4H)-one

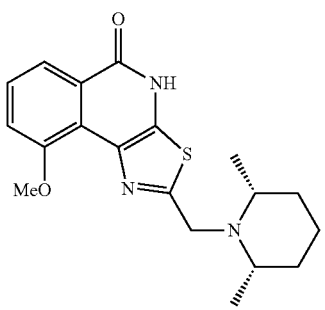 [SMILES: COc1cccc2c(=O)[nH]c3sc(CN4[C@H](C)CCC[C@@H]4C)nc3c12]

The title compound was prepared according to the procedure of Example 5, Step 1 above except that (2S,6R)-2,6-dimethylpiperidine was used in place of morpholine.

MS (ES$^+$) m/z 358 (M+H).

Step 2

2-{[(2R,6S)-2,6-Dimethylpiperidin-1-yl]methyl}-9-hydroxy[1,3]thiazolo[5,4-c]isoquinolin-5(4H)-one

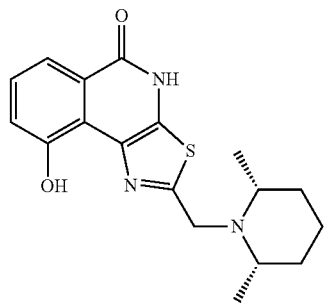 [SMILES: C[C@@H]1CCC[C@H](C)N1Cc1nc2c([nH]c(=O)c3cccc(O)c32)s1]

The title compound was prepared according to Example 4, Step 4 using the product of Step 1 above as the starting material.

MS (ES$^+$) m/z 344 (M+H).

Example 14

Functional Assessment of Human PARP-1 Enzymatic Activity

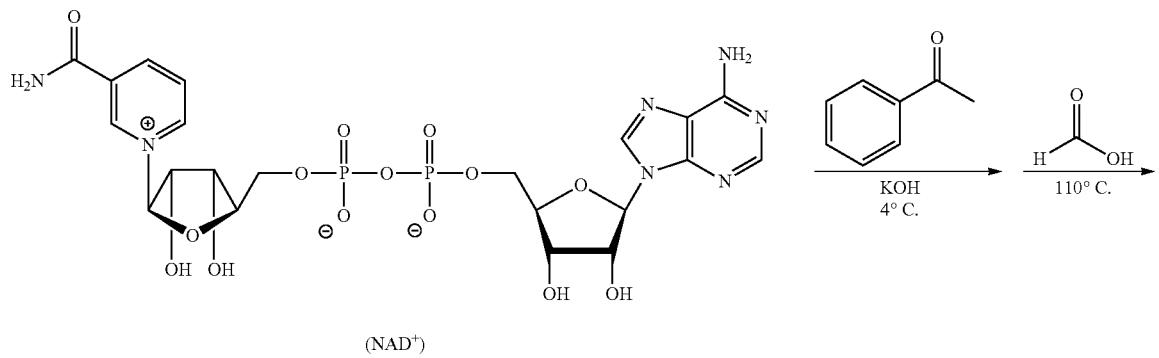

(NAD$^+$)

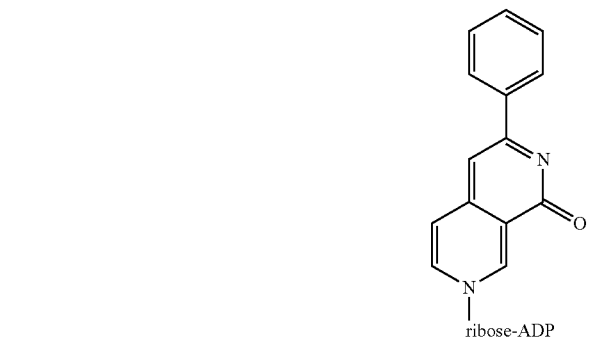

1 fluorescece excitation at 372 nm, emmision at 444 nm

Materials and Reagents:

hrPARP-1 (human recombinant, Trevigen), Activated DNA (Sigma), 6(5H)-phenanthridinone (PND), (Sigma), NAD+(Calbiochem), PARP-1 assay buffer (50 mM Tris, 2 mM MgCl2, pH 8.0), 20% acetophenone in EtOH, 2 M KOH 88% formic acid, 110° C. oven, Flexstation Plate Reader.

Procedure:

Compound plates were prepared by making a series of 1:3 dilutions for each tested compound, 10 steps of each at 20 μL in DMSO starting from a concentration of 5 mM. NAD+ (39 μL of a 6.4 μM solution) were added to each well of a 96-well flat bottom fluorescent assay plate. Test compound (1 μL) was added to each well. To initiate the reaction, 10 μL of PARP (contains 5 U of PARP and 75 μg/mL activated DNA) was added with a final 1 U hrPARP-1, 15 μg/mL activated DNA and 5 μM of NAD+. The highest concentration used for test compounds was 100 μM. The plates were incubated at room temperature on a shaker. After 20 min, 20 μL of 2 M KOH and 20 μL of 20% acetophenone were added. The plate was incubated 10 min. at 4° C., and 90 μL of 88% formic acid was added. After incubating in a 110° C. oven for 5 min, the plate was cooled to room temperature and read of a Flexstation Plate Reader (excitation at 360 nm, emission at 445 nm).

Analysis of Results:

LSW data analysis software was used to generate PARP-1 $IC_{50}$s. The results are presented in Table 1.

TABLE 1

| EXAMPLE # | $IC_{50}$ (nM) |
|---|---|
| 1 | 378 |
| 2 | 414 |
| 3 | 358 |
| 4 | 99 |
| 5 | 18.3 |
| 6 | 1366 |
| 7 | 111 |
| 8 | 223 |
| 9 | 2448 |
| 10 | 3088 |
| 11 | 747 |
| 12 | 3505 |
| 13 | 1500 |

When ranges are used herein for physical properties, such as molecular weight, or chemical properties, such as chemical formulae, all combinations and subcombinations of ranges specific embodiments therein are intended to be included.

The disclosures of each patent, patent application and publication cited or described in this document are hereby incorporated herein by reference, in its entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:

1. A method of treating a cancer in a subject by inhibiting poly(ADP-ribose) polymerase (PARP), wherein the cancer is selected from breast cancer, ovarian cancer, pancreatic cancer, prostate cancer, lung cancer, multiple myeloma, leukemia and colon cancer, the method comprising administering to the subject an effective amount of a compound of formula I:

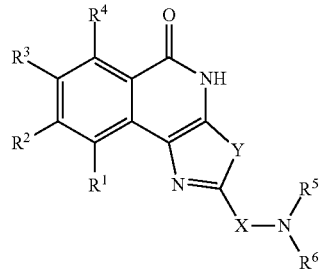

Formula I wherein:
X is $C_1$-$C_9$ alkylene, $C_2$-$C_9$ alkenylene, or $C_2$-$C_9$ alkynylene;
Y is O or S;
$R^1$ is hydrogen, hydroxy, or $OR^7$;
$R^2$, $R^3$, and $R^4$ are independently hydrogen;
$R^5$ and $R^6$ are each, independently, $C_1$-$C_6$ alkyl, wherein the alkyl is optionally substituted with one or more groups independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, and halogen; or
$R^5$ and $R^6$ together with the nitrogen to which they are attached form a saturated, partially unsaturated, or unsaturated 3 to 12 membered monocyclic or bicyclic heterocyclic ring optionally comprising from one to three additional ring heteroatoms independently selected from N, O, and S, the remainder of the ring atoms are carbon atoms; and
$R^7$ is $C_1$-$C_6$ alkyl, $C_2$-$C_6$ alkenyl, or $C_3$-$C_7$ cycloalkyl wherein the alkyl, alkenyl, and rings of the cycloalkyl are optionally substituted with one or more groups independently selected from hydroxy, $C_1$-$C_4$ alkoxy, —$CO_2H$, $C_1$-$C_6$ alkoxycarbonyl, $NH_2$, $C_1$-$C_6$ mono- or dialkylamino, and halogen;
or a pharmaceutically acceptable salt form thereof.

2. The method of claim 1, wherein $R^1$ is hydrogen or hydroxy, or a pharmaceutically acceptable salt form thereof.

3. The method of claim 1, wherein the compound is according to Formula III:

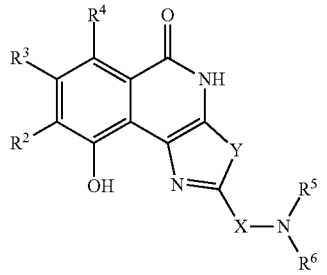

Formula III or a pharmaceutically acceptable salt form thereof.

4. The method of claim 1, wherein X is $C_1$-$C_3$ alkylene, $C_2$-$C_3$ alkenylene, or $C_2$-$C_3$ alkynylene.

5. The method of claim 1, wherein Y is O.

6. The method of claim 1, wherein Y is S.

7. The method of claim 1, wherein $R^5$ and $R^6$ are each, independently, $C_1$-$C_6$ alkyl.

8. The method of claim 1, wherein $R^5$ and $R^6$ together with the nitrogen to which they are attached form a saturated monocyclic heterocyclic ring optionally comprising from one to three additional ring heteroatoms selected from N, O, and S, and the remainder of the ring atoms are carbon atoms.

9. The method of claim 1, wherein $R^5$ and $R^6$ together with the nitrogen to which they are attached form piperidine, morpholine, pyrrolidine, homopiperidine, aziridine, or azetidine.

10. The method of claim 1, wherein X is $C_2$-$C_3$ alkynylene.

11. The method of claim 1, wherein:
Y is S;
X is $C_1$-$C_3$ alkylene; and
$R^5$ and $R^6$ are each, independently, $C_1$-$C_6$ alkyl.

12. The method of claim 1, wherein:
Y is O;
X is $C_1$-$C_3$ alkylene; and
$R^5$ and $R^6$ are each, independently, $C_1$-$C_6$ alkyl.

13. The method of claim 1, wherein the compound is selected from:

2-[(Dimethylamino)methyl[1,3]thiazolo[5,4-c]isoquinolin-5(4H)-one;

2-[3-(Dimethylamino)prop-1-yn-1-yl][1,3]thiazolo[5,4-c]isoquinolin-5(4H)-one;

2-(2-(Dimethylamino)ethyl)thiazolo[5,4-c]isoquinolin-5(4H)-one;

2-((Dimethylamino)methyl)-9-hydroxythiazolo[5,4-c]isoquinolin-5(4H)-one;

9-Hydroxy-2-(morpholin-4-ylmethyl)[1,3]thiazolo[5,4-c]isoquinolin-5(4H)-one;

9-Hydroxy-2-(piperidin-1-ylmethyl)[1,3]thiazolo[5,4-c]isoquinolin-5(4H)-one;

9-Hydroxy-2-(pyrrolidin-1-ylmethyl)[1,3]thiazolo[5,4-c]isoquinolin-5(4H)-one;

2-{[(3R)-3-(dimethylamino)pyrrolidin-1-yl]methyl}-9-hydroxy[1,3]thiazolo[5,4-c]isoquinolin-5(4H)-one;

9-Hydroxy-2-(octahydroquinolin-1(2H)-ylmethyl)[1,3]thiazolo[5,4-c]isoquinolin-5(4H)-one;

2-{[(2R,6S)-2,6-Dimethylmorpholin-4-yl]methyl}-9-hydroxy[1,3]thiazolo[5,4-c]isoquinolin-5(4H)-one;

9-Hydroxy-2-[(2-methylpyrrolidin-1-yl)methyl][1,3]thiazolo[5,4-c]isoquinolin-5(4H)-one;

9-Hydroxy-2-{[(2R)-2-(trifluoromethyl)pyrrolidin-1-yl]methyl}[1,3]thiazolo[5,4-c]isoquinolin-5(4H)-one; and 2-{[(2R,6S)-2,6-Dimethylpiperidin-1-yl]methyl}-9-hydroxy[1,3]thiazolo[5,4-c]isoquinolin-5(4H)-one; or a pharmaceutically acceptable salt form thereof.

\* \* \* \* \*